United States Patent
Alness et al.

(10) Patent No.: US 6,350,409 B1
(45) Date of Patent: Feb. 26, 2002

(54) HEAT DISINFECTION OF SEEDS

(75) Inventors: Kenneth Alness; Sven Andersson; Sven Bergman, all of Sverige (SE)

(73) Assignee: Svenska Lantmännen, riksförbund ek. för., Stockholm (SE)

(*) Notice: Subject to any disclaimer, the term of this patent is extended or adjusted under 35 U.S.C. 154(b) by 0 days.

(21) Appl. No.: 09/147,116

(22) PCT Filed: Apr. 10, 1997

(86) PCT No.: PCT/SE97/00594

§ 371 Date: Apr. 23, 1999

§ 102(e) Date: Apr. 23, 1999

(87) PCT Pub. No.: WO97/38734

PCT Pub. Date: Oct. 23, 1997

(30) Foreign Application Priority Data

Apr. 14, 1996 (SE) .................................................. 9601382

(51) Int. Cl.[7] .................................................. A61L 11/00
(52) U.S. Cl. .................. 422/1; 422/1; 422/4; 34/28; 34/34; 34/35; 34/86; 34/168; 426/507; 426/508; 426/511; 426/521
(58) Field of Search .................... 34/28, 34, 35, 34/86, 168; 422/1, 4; 426/507, 508, 511, 521

(56) References Cited

U.S. PATENT DOCUMENTS 3,973,047 A * 8/1976 Linaberry et al. .......... 426/473
4,479,309 A * 10/1984 Tolson ........................ 34/28
4,973,484 A * 11/1990 Pierik ........................ 34/86

FOREIGN PATENT DOCUMENTS

| DD | 297333 A5 | 1/1992 |
| EP | 0196464 A2 | 10/1986 |
| EP | 0622085 A1 | 11/1994 |
| JP | 58-111667 A | 7/1983 |

OTHER PUBLICATIONS

Merriam Webster's Collegiate Dictionary Tenth Edition, 1993, pp. 748–749 and 506.*
Forskningnytt, Nr. 1, "Värmedehandling mot ustädesburna svampsjukdomar", 1996, p. 6.
Bergman, Svenska vä xtskyddskonferensen/Swedish Crop Protection C, Uppsala Institutionione, Artikel 34 (1993).
MacKay et al., Plant Pathology, vol. 32, pp. 385–393 (1983).

* cited by examiner

Primary Examiner—Robert J. Warden, Sr.
Assistant Examiner—Imad Soubra
(74) Attorney, Agent, or Firm—Bacon & Thomas

(57) ABSTRACT

The invention relates to a heat treatment process for disinfection of seeds from pathogens and other undesirable fungi and bacteria, the process being characterized by supply to the seeds non water-borne heat while regulating the treatment time and temperature with regard to the condition and moisture content of the seeds in such a way that the seeds are heated from outside and in, while evaporation of moisture from the surface of the seed, and owing to that, cooling of the same is prevented and no changes in the moisture content occur.

18 Claims, 1 Drawing Sheet

HEAT DISINFECTION OF SEEDS

FIELD OF INVENTION

The present invention relates to a heat treatment process for disinfection of seeds from pathogens as well as other non-desirable fungi and bacteria. The process is applicable to seeds of crops from forestry, horticulture and agriculture and is particularly applicable to seed of different crops used in agriculture and horticulture. The invention will be further described below with reference to application of the heat treatment process to cereal seed, but the invention is not restricted to said application.

BACKGROUND OF THE INVENTION

Seed-borne pathogens, e.g. pathogenic fungi in cereals, every year cause great economic losses, they reduce the crop yield, deteriorate its quality and make storage of e.g. potatoe more difficult. For ecological cultivators, it is very essential that the seed is free from pathogens since control is difficult to effect during the cultivation season. The need for an ecological disinfection method against seed-borne pathogens is therefore very great. Each year large quantities of cereals are treated chemically (more than 90% of autumn-sown grain; about 40–50% of spring-sown grain) against seed-borne fungal diseases, in order to achieve a healthier crop which, owing to that, needs less or no chemical control during the cultivation season. Most cultivators are aiming at reducing the use of chemical agents for economic, environmental and working-health reasons. Therefore, there is a great need for replacing a great part of the chemical seed treatment methods by a disinfection method that does not require chemicals.

The Prior Art

In the 1950's and 1960's hot water treatment was used as disinfection method in order to control loose smut in barley and wheat. The treatment was as follows (Persson, 1990):

The seed was soaked in water for about 3 hours.

It was picked up and was allowed to drain.

The wheat was placed in water of 53° C. and the barley in water of 51° C., for 5 minutes.

The seed was transferred to cold water for cooling, for 5 minutes.

The seed was dried.

The stated disinfection method was labour-intensive and was driven out of competition by new chemical seed treatment agents, mainly for two reasons. On one hand, the known hot water treatment method gave an uncertain effect and, on the other hand, it was costly because, above all, it was expensive to dry the seed after the treatment.

Experiments with hot water treatment of cereal seed has shown good effect against loose smut (*Ustilago nuda*), leaf stripe (*Drechslera graminea*), and net blotch (*Drechslera teres*) on barley, loose smut (*Ustilago tritici*), snow mould (*Microdochium nivale*), leaf and glume blotch (*Stagonospora nodorum*), and yellow leaf spot (*Drechslera tritici-repentis*) on wheat, loose smut (*Ustilago avenae*) and leaf stripe (*Drechslera avenae*) on oats as well as snow mould on rye (Bergman, 1993, 1994, 1996a, 1996b). However, in this study a great problem has been the high costs for drying the kernels after the treatment; the moisture content may be above 50% after the treatment. The cereal kernels have to be dried down to a moisture content below 15% in order for them to be stored without deterioration.

In order to avoid the costs for drying of the seed after hot water treatment, also dry hot air has been tested, however with poor results. Microwave treatment has also been tested, but without success. The explanation for this may be that, by treatment with microwaves, heat is generated inside the seed where the sensitive embryo is localized while most pathogens are on the surface of the kernel where less heat is generated. Water steam has also been tested in experiments but the high temperature gives a narrow band between the effect on pathogens and a harmful effect on the germination.

As regards the prior art, reference is also made to DD 217407, DD 297333, EP 0196464, EP 0622085, GB 1535926, GB 2150803, FR 1260436, JP 58111667, SU 422368, SU 760905 and U.S. Pat. No. 4,633,611.

Purpose of the Invention

The general purpose of the invention is to provide an economically interesting disinfection method in order to reduce the presence of seed-borne pathogens, with as small risk as possible for the environment; this is done in order to reduce the use of chemical controlling agents while maintaining good production possibilities.

Another purpose is to disinfect seeds by means of a carefully controlled heating without permitting changes in moisture content.

SHORT DESCRIPTION OF THE INVENTION

The purposes of the invention are achieved by a heat treatment process for disinfection of seeds from pathogens as well as other non-desirable fungi and bacteria, the process being characterized by supplying to the seeds non-water-borne heat while regulating the treatment time and temperature, with regard to the condition and moisture content of the seeds, in such a way that the seeds are heated from outside and in, while evaporation of moisture from the surface of the seed and, owing to that, cooling of the same is prevented. According to one embodiment of the invention, the heat supply is accomplished by contact transfer of heat to the seeds enclosed on a band conveyor, and according to a preferred embodiment the heat supply is accomplished by hot air having an air moisture content that prevents a decrease or increase of the moisture content of the seeds.

The seeds are e.g. kernels of cereals and potatoes.

By "seed" is herein meant the reproductive body of the seed-plants. By "kernels" is herein meant seed-kernels as regards cereals, i.e. the fruits of the cereals, and seed potatoes as regards potatoe.

SHORT DESCRIPTION OF THE FIGURES OF THE DRAWING

In the enclosed drawing, the figures show the following.

DETAILED DESCRIPTION OF THE INVENTION

Figure 1:
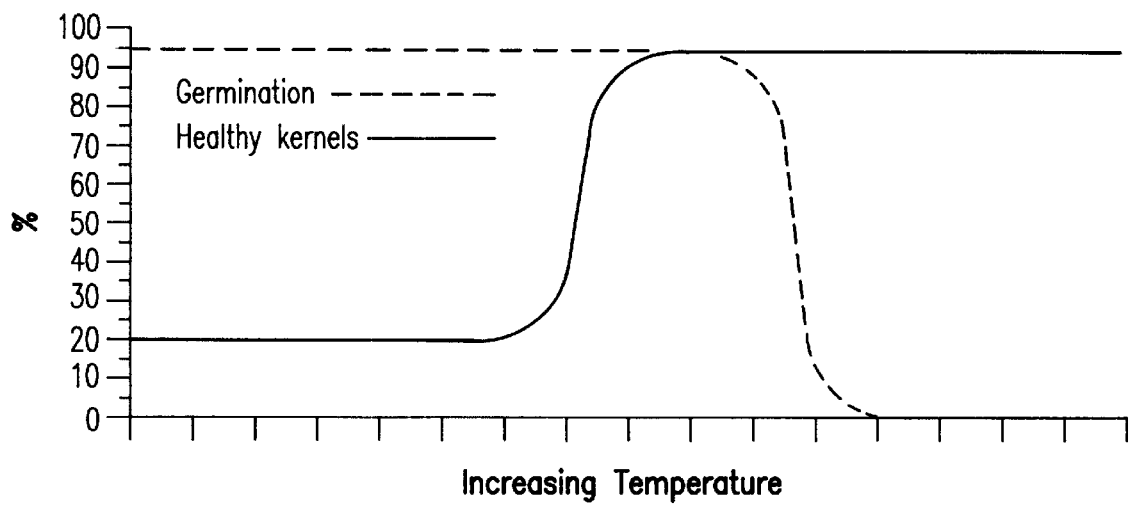
FIG. 1 shows the percentage effect of heat treatment on the germination and healthiness of the seed with increasing treatment temperature.

An effective heat disinfection requires constant and exact heat supply for an exact time period. The principle of heat treatment of seeds can be described according to FIG. 1. The interesting interval is where the treatment disinfects the seed from pathogens without a decrease in germination. If the treatment temperature is too low, the pathogens will survive, and if the temperature is too high, the seeds will die.

The greater difference between the death of the pathogen and the host, the better chance for a successful heat treatment. The following factors may influence the sensitivity to heat treatment (Baker, 1962):

the moisture content of the treated material; the higher moisture content, the more sensitive.

possible resting stage, e.g. germination rest; non-resting material is more sensitive.

the age and viability of the seed; older and weaker material is more sensitive.

the condition of possible protective coats; cracks in the seed-coat make the seed more sensitive.

the temperature during the growing time; low temperature during the growing time increases the sensibility.

the size of treated material; the smaller, the more sensitive.

variation in variety.

As mentioned above, the disadvantage of hot water treatment according to the old method is that the moisture content of the seeds after the treatment may be above 50%, which means that the seeds, upon treatment, must be dried down to a storable moisture content, which is rather expensive. The heat treatment method according to the invention provides an effectively improved and better controlled heating process. With the heat treatment process according to the present invention one achieves such a low moisture content after treatment that no drying is needed. The process according to the invention is based on the inventive idea to disinfect the seed by means of a carefully controlled heating without permitting drying, i.e. evaporation from the seeds so that the surface of the seed is cooled, or an increase of the moisture content since most of the pathogens are located in the surface layer of the seed.

As mentioned above, the known technique with hot water treatment of seed is associated with certain disadvantages and the present invention is based upon the understanding that an exact control of the heat treatment process would provide a much higher efficiency than an uneven treatment and that a high precision control of the heat treatment process can today be achieved with available technique. The process of the invention thus involves treatment of seeds with heat in the manner stated in claim 1, a preferred embodiment involving treatment of the seeds with tempered air of high moisture content.

A feature of the process according to the present invention is the supply to the seeds of non-water-borne heat while regulating the treatment time and temperature, dependent on the condition and moisture content of the seeds.

Figure 2:
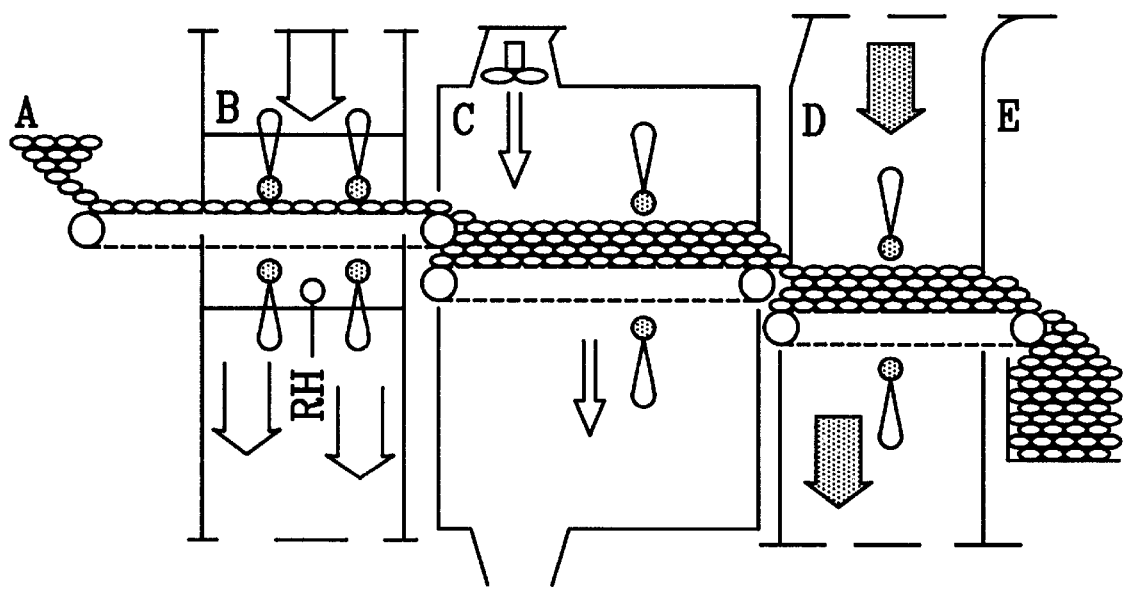
FIG. 2 is a schematic description of an embodiment of the process according to the invention.

The process of the invention is further described below with reference to the embodiment shown in FIG. 2. This embodiment of the process according to the invention is carried out continuously in five phases which are the following:

A. a feeding phase where the layer thickness of the seeds fed is regulated so that the subsequent heating phase guarantees a homogeneous heating;

B. a heating phase where the seeds, by supply of hot air, are heated to a predetermined treatment temperature, the heating phase being as short as possible and being performed so that the moisture content of the seeds will not be changed. Evaporation, if any, from the seeds results in energy being used for the evaporation instead of for heating and thus counteracts an efficient heating. The time in this treatment phase must, however, be long enough to allow the seeds to reach the predetermined treatment temperature. This phase is the most sensitive as regards both the quality and the capacity;

C. a treatment phase where the seeds are treated by keeping them warm during a calculated treatment time with constant temperature and moisture content;

D. a cooling phase where the seeds are rapidly cooled in order to control the treatment time; and E. an output phase where the disinfected seeds are withdrawn.

A suitable moisture content of the hot air introduced in phase B and C would be 60–90%, dependent on the kind of seed and its moisture content.

The treatment time in phase C is dependant of the kind of seed to be treated and the pathogen to be eliminated. Successful experiments have been carried out with a treatment time below 10 minutes with cereals (barley). In certain cases, dependant on the type of seed and pathogen, treatment times up to 10 minutes or even above may be required.

The temperature in phase B and C is dependent of the moisture content of the seeds fed and the pathogen from which the seeds shall be disinfected. The temperature may, when a temperature suitable for the treatment has been established, be regulated so well that it is maintained within a narrow range. In the above-mentioned experiments with barley where the treatment time was less than 5 minutes, use was made of a temperature of 65–67° C. and the treatment air had a moisture content of above 70%.

The energy consumption may be reduced to a minimum by using a closed system where the heating energy is recirculated during a cooling process.

Temperature changes in the seed and their effect on germination are essential to note (Nellist, 1978; Nellist & Bruce, 1995).

The success of the process according to the invention is based upon the fact that one, with high precision, controls the heat treatment so that one gets no evaporation from the surface of the seed and one does not obtain any change of moisture content, while at the same time keeping the heat treatment time period so short and adjusting the treatment temperature in such a way that no protein denaturation and no germination deterioration is obtained.

EXAMPLE

In the experiments reported below, infected seed of each crop was used and each batch of infected crop was analysed with regard to degree of infection, moisture content and percentage germination before carrying out any treatment. For these analyses conventional methods were used according to e.g. the ISTA handbook (International Rules for Seed Testing, 1993).

For analysis of the percentage germination both sand, paper and soil can be used, where appropriate. For determination of the degree of infection in cereal a method can be used based upon the osmotic blotter method (Joelson, 1983), in parallel with other methods. This is a rapid and simple method which is particularly suitable for detecting pathogenic fungi belonging to the Drechslera genus. In this determination method, the kernels are placed on moist absorbing paper in a flat transparent container. The paper is dipped into a sugar syrup (135 g/l of tap water) and is allowed to drain. The container is placed in a chamber with 12 hours of light at 25–28° C., alternatively with 12 hours of darkness at 18–20° C. The osmotic pressure of the solution prevents the kernels from growing but allows the fungus to begin to grow. The fungi that are reduced and stressed begin to release specific substances that can be studied on the paper. Symptoms of Drechslera spp. can be studied after 7 days.

After treatment of the seed, the same analysis methods are used as described above. In order to finally evaluate the treatment effects, the treated seed has been sown in field experiments. The results of these are shown below.

Experiments with the new treatment method according to the invention has so far been made with barley seed that has a natural infection of *Drechslera teres, Drechslera graminea* and *Ustilago nuda*.

The results of field experiments, which have been carried out during 1995, are shown below. In comparison the results for untreated seed, fungicide treated seed and seed treated with hot water are given (only Table 1).

TABLE 1

Field experiments in 1995, the country of Östergötland. Germination change and disinfection effect of different seed treatment methods against leaf strip (*Drechslera graminea*), net blotch (*Drechslera teres*) and loose smut (*Ustilago nuda*) in barley

| Treatment | relative % Germination | seedlings/ $m^2$ Germination | relative % D. graminea | seedlings/ $m^2$ D. graminea | relative % D. teres | seedlings/ $m^2$ D. teres | relative % U. nuda | seedlings/ $m^2$ U. nuda |
|---|---|---|---|---|---|---|---|---|
| untreated | 100 | 372 | 100 | 42 | 100 | 11 | 100 | 46 |
| Panoctine Plus* | 107 | 397 | 0 | 0 | 0 | 0 | 62 | 29 |
| hot water** | 83 | 309 | 49 | 22 | 0 | 0 | 28 | 13 |
| method X*** | 95 | 353 | 0 | 0 | 0 | 0 | 55 | 25 |
| | LSD = 0.05; 54.4 | | LSD = 0.05; 17.3 | | LSD 0.05 = 3.7 | | LSD 0.05 = 14.1 | |

*=guazatine acetate (150 g/l) + imizalil (10 g/l)
**=presoak; draining, hot water for 5 minutes at 52° C.; cold water for 5 minutes; drying.
***=the novel heat treatment method according to the invention.

TABLE 2

Field experiments in 1995, the county of Stockholm. Germination change and disinfection effect of different seed treatment methods against leaf stripe (*Drechslera graminea*) and loose smut (*Ustilago nuda*) in barley

| Treatment | relative % Germination | seedlings/ $m^2$ Germination | relative % D. graminea | seedlings/ $m^2$ D. graminea | relative % U. nuda | smutted heads/100 $m^2$ U. nuda |
|---|---|---|---|---|---|---|
| untreated | 100 | 323 | 100 | 42 | 100 | 75 |
| Panoctine Plus* | 108 | 348 | 2 | 1 | 70 | 52 |
| Method X** | 96 | 309 | 4 | 2 | 76 | 57 |
| | LSD = 0.05; 50.7 | | LSD = 0.05; 7.9 | | LSD = 0.05 = 36.5 | |

*= guazatine acetate (150 g/l) + imizalil (10 g/l)
**= the novel heat treatment method according to the invention.

TABLE 3

Field experiments in 1995, the county of Stockholm. Germination change and disinfection effect of different seed treatment methods against net blotch (*Drechslera teres*) in barley

| Treatment | relative % Germination | seedlings/ $m^2$ Germination | relative % D. teres | seedlings/ $m^2$ D. teres |
|---|---|---|---|---|
| untreated | 100 | 389 | 100 | 46 |
| Panoctine Plus* | 95 | 370 | 4 | 2 |
| method X** | 97 | 376 | 0 | 0 |
| | LSD = 0.05; 67.9 | | LSD 0.05 = 5.5 | |

*= guazatine acetate (150 g/l) + imizalil (10 g/l)
**= the novel heat treatment method according to the invention.

The results show that the heat treatment method according to the invention compares well with fungicide treatment and is superior to the hot water treatment method.

The heat treatment method according to the present invention has consequently a great potential. In 1992/93 140,000 tons of State-certified seed were sold in Sweden (cereal seed, etc.) of which 50% was chemically treated seed (Statistics Sweden, 1995). Supposing that 10% of the production in farming will be ecologically produced in the year 2000, this means that 14,000 tons of seed will be needed for ecological production and possibly a larger part of the seed must be disinfected (supposing 75%, that makes 10,500 tons). A further estimation can be made of how much conventionally treated seed that can be replaced by heat disinfected seed, and, therefore, the technique has a great potential.

A first preliminary estimation of the costs for heating is SEK 0.10–0.15 per kg. This corresponds to the preparation cost in conventional seed treatment and it is estimated that the operating and equipment costs will not differ very much from conventional seed treatment. The results above show that the heat treatment method according to the invention compares well with fungicide treatment, and, therefore, the method according to the invention offers an extremely good alternative from an economic point of view and especially from an ecological and environmental point of view.

The heat treatment method according to the present invention can also be used in applications other than those described above when it is desirable and of importance to disinfect the seeds from other undesirable fungi and bacteria without negatively affecting the germination, e.g. in beer production. A further application of the process is for disinfection of seed potatoes and seeds for garden trade, e.g. carrot seed, and the forestry trade.

As regards the known technique for disinfection of seed potatoes, reference is made to Burnett, 1990; Machay and Shipton, 1983; and Van der Zaag, 1956.

LITTERATURE

Baker, K. F. 1962. Thermotherapy of Planting Material. Phytopathology 52, 1244–1920, 1962.

Bergman, S., 1993. Heat treatment as disinfection method against seed-borne fungal diseases on cereals, 34:th Swedish Crop Protection Conference.

Bergman, S., 1994. Heat treatment as disinfection method against seed-borne fungal diseases on cereals. Conference Ecological Agriculture, Uppsala, Sweden, Nov. 23–24, 1993, Ecological agriculture, No. 17.

Bergman, S., 1996a. Heat treatment as disinfection method against seed-borne fungal diseases on cereals and potatoes. Conference Ecological Agriculture, Uppsala, Sweden, Nov. 7–8, 1995, Ecological agriculture, No. 20.

Bergman, S., 1996b. Heat treatment against seed-borne fungal diseases. Forskningsnytt om oekologisk landbruk i Norden, nr 2.

Burnett, E. T., Dashwood, P. E. & Perombel on, M.C.M. 1990. Control of blackleg and tuber borne fungal diseases by hot water treatment of seed tubers, 11th Triennial Conference, European Association for Potato Research, EAPR-Abstracts, 441–442.

International Seed Testing Association (1993), Seed Science and Technology, 21, Supplement, Rules.

Joelsson, G., The osmotic method—a method for rapid determination of seed-borne fungi. International Seed Testing Association, $20^{th}$ ISTA Congress, Ottawa, Jun. 17–25, 1983.

Mackay, J. M. & Shipton, P. J. 1983. Heat treatment for control of potato blackleg (*Erwinia carotovora* subs *atroseptic*) and other diseases. Plant Path. 32, 385–393.

Nellist, M. E., Safe Temperatures for Drying Grain. National Institute of Agricultural Engineering, Report No. 29, January 1978.

Nellist, M. E. & Bruce, D. M., Heated-Air Grain Drying. Chapter 16 in Stored-Grain Ecosystems, ed. by Jayas, D. S., White, N. D. G. & Muir, W. E., 609–659, 1995.

Persson, G. Hot water treatment of model Weibull, 1955. Letter to Lennart Johnsson, March 1990.

Statistics Sweden, 1995. Yearbook of Agricultural Statistics 1995.

Van der Zaag, D. A. Overwintering an Epidemiologi van *Phytophthora infestans*. Wageningen 1956.

What is claimed is:

1. Heat treatment process for disinfection of seeds from pathogens and other undesirable fungi and bacteria, characterised by supplying to the seeds non-water-borne heat while regulating the treatment time and temperature with regard to the condition and moisture content of the seeds, in such a way that the seeds are heated from outside and in while evaporation of moisture from the surface of the seed and, owing to that, cooling of the same is prevented and no changes in the moisture content occur.

2. The process according to claim 1, characterised in that the seeds are kernels of cereals.

3. The process according to claim 2, characterized in that the heat supply is accomplished by contact transfer to the seeds enclosed on a band conveyor.

4. The process according to claim 2, characterized in that it is carried out continuously in five phases as follows:
   A. a feeding phase where the layer thickness of the seeds fed is regulated so that the subsequent heating phase guarantees a homogenous heating;
   B. a heating phase where the seeds, by supply of hot air, are heated to a pre-determined treatment temperature, the heating phase being as short as possible and being carried out so that the moisture content of the seeds are not changed;
   C. a treatment phase where the seeds are treated by keeping them warm during a calculated treatment time with constant temperature and moisture content;
   D. a cooling phase where the seeds are rapidly cooled in order to control the treatment time; and
   E. an output phase where the seeds are withdrawn.

5. The process according to claim 1, characterised in that the heat supply is accomplished by contact transfer to the seeds enclosed on a band conveyor.

6. The process according to claim 1, characterised in that it is carried out continuously in five phases as follows:
   A. a feeding phase where the layer thickness of the seeds fed is regulated so that the subsequent heating phase guarantees a homogeneous heating;
   B. a heating phase where the seeds, by supply of hot air, are heated to a pre-determined treatment temperature, the heating phase being as short as possible and being carried out so that the moisture content of the seeds are not changed;
   C. a treatment phase where the seeds are treated by keeping them warm during a calculated treatment time with constant temperature and moisture content;
   D. a cooling phase where the seeds are rapidly cooled in order to control the treatment time; and
   E. an output phase where the seeds are withdrawn.

7. The process according to claim 6, characterised in that the heat supply is made by hot air which has a moisture content that prevents a decrease or increase of the moisture content of the seeds.

8. The process according to claim 6, wherein the treatment disinfects the seeds from pathogens without a decrease in germination rate of the seeds.

9. The process according to claim 8, wherein the non-water-borne heat is hot air.

10. The process according to claim 6, wherein the non-water-borne heat is hot air.

11. The process of claim 8, wherein the hot air has a moisture content of 60–90%.

12. The process according to claim 11, wherein the treatment time was less than 5 minutes, the temperature of the hot air was 65–67° C. and the treatment air had a moisture content of above 70%.

13. The process according to claim 10, wherein the temperature, moisture content of the heated air and temperature are controlled so that there is no evaporation from the surface of the seed and no change of moisture content in the seed with the accompanying heat treatment so that no protein denaturation or no germination deterioration is obtained.

14. The process according to claim 1, wherein the treatment disinfects the seeds from pathogens without a decrease in germination rate of the seeds.

15. The process according to claim 14, wherein the non-water-borne heat is hot air.

16. The process of claim 15, wherein the hot air has a moisture content of 60–90%.

17. The process according to claim 1, wherein the non-water-borne heat is hot air.

18. The process according to claim 17, wherein the temperature, moisture content of the heated air and temperature are controlled so that there is no evaporation from the surface of the seed and no change of moisture content in the seed with the accompanying heat treatment so that no protein denaturation or no germination deterioration is obtained.

* * * * *